United States Patent [19]

Bauer et al.

[11] Patent Number: 4,871,754
[45] Date of Patent: Oct. 3, 1989

[54] AQUEOUS FORMULATION OF 1,2-BENZISOTHIAZOLIN-3-ONE

[75] Inventors: Wolfgang Bauer, Maintal; Willi Steckelberg, Hofheim, both of Fed. Rep. of Germany

[73] Assignee: Cassella Aktiengesellschaft, Frankfurt am Main, Fed. Rep. of Germany

[21] Appl. No.: 943,145

[22] Filed: Dec. 18, 1986

[30] Foreign Application Priority Data

Jan. 8, 1986 [DE] Fed. Rep. of Germany ....... 3600271

[51] Int. Cl.$^4$ ............................................. A01N 43/80
[52] U.S. Cl. ................................................... 514/373
[58] Field of Search ........................................ 514/373

[56] References Cited

U.S. PATENT DOCUMENTS

| 3,065,123 | 11/1962 | Hinton et al. | 514/373 X |
| 4,150,026 | 4/1979 | Miller et al. | 260/299 |
| 4,188,376 | 2/1980 | Payne et al. | 514/971 X |

FOREIGN PATENT DOCUMENTS 1191253  5/1970  United Kingdom .
1330531  9/1973  United Kingdom .

OTHER PUBLICATIONS

"Mycotoxine aus Schimmelpilzen", (Mycotoxines from Molds), by Burchard Franck in Angewandte Chemie (Applied Chemistry), International Edition, pp. 493–505.

Karl Heinz Wallhausser: Praxis der Sterilisation, Desinfektion–Konservierung–Keimidentifizierung–Betriebshygiene, (Practice for Sterilization Disinfection–-Preservation Germ Identification–Industrial Hygiene), Georg Thieme Verlag, Stuttgart/New York, 3rd revised and enlarged edition, 1984, pp. 460 and 461.

Kirk–Othmer, Encyclopedia of Chemical Technology, 3rd ed., vol. 7, pp. 170 and 171.

*Primary Examiner*—Leonard Schenkman
*Attorney, Agent, or Firm*—Connolly and Hutz

[57] ABSTRACT

Aqueous solutions are protected from infestation by micro-organisms by use of a biocide which is an aqueous formulation of the lithium salt of 1,2-benzisothiazolin-3-one.

8 Claims, No Drawings

AQUEOUS FORMULATION OF 1,2-BENZISOTHIAZOLIN-3-ONE

On the basis of its bactericidal and fungicidal properties, 1,2-benzisothiazolin-3-one is used in industry as a biocide for protecting aqueous media from infection by microorganisms. For these intended uses, it is desirable for the 1,2-benzisothiazolin-3-one to be in the form of a liquid formulation which, when left to stand and when the temperature is reduced to 0 to 5° C., shows no precipitates, no settling and no solidification or losses in activity.

It is already known that crude 1,2-benzisothiazolin-3-one obtained during synthesis in the form of an aqueous dispersion can be used to prepare liquid formulations of 1,2-benzisothiazolin-3-one. However, such aqueous dispersions are not stable on storage, since settling occurs when they are left to stand.

Liquid formulations of 1,2-benzisothiazolin-3-one which consist of solutions of 1,2-benzisothiazolin-3-one in an amine or amine mixture are also known (British Patent Specification 1,191,253 and 1,330,531). However, these formulations are unacceptable for certain intended uses because of their amine content.

It was furthermore known from German Patent A1-2,840,273, (corresponding to USP 4,188,376), page 3, last but one paragraph, that 1,2-benzisothiazolin-3-one forms salts with alkali metals and that these are water-soluble and that solutions of crude 1,2-benzisothiazolin-3-one in propylene glycol or diethylene glycol can be prepared and added to water in order to prepare solutions. However, it was also known from the literature reference mentioned that stable solutions with a concentration sufficient for commercial purposes, that is to say a content of 1,2-benzisothiazolin-3-one of not less than approximately 5% by weight, cannot be prepared by these processes. According to German Patent A1-2,840,273, the storage stability of such liquid preparations of 1,2-benzisothiazolin-3-one can be improved by adding certain hydroxylic organic solvents. The liquid composition according to German Patent A1-2,840,273 containing 1,2-benzisothiazolin-3-one contains 5 to 50% by weight of an alkali metal salt of crude 1,2-benzisothiazolin-3-one in a hydroxylic organic solvent which is selected from at least one of the following: dipropylene glycol, tripropylene glycol, polypropylene glycols, polyethylene glycols, lower alkyl carbitols, methanol, ethanol and mixtures of at least one of these solvents and water. The sodium salt is mentioned in German Patent A1-2,840,273 as the preferred alkali metal salt of crude 1,2-benzisothiazolin-3-one, and is also used in all the embodiment examples. In addition, the lithium salt is also mentioned at a single point: ("the alkali metal salt of crude BIT can be, for example, the lithium salt but in particular the sodium salt").

According to German Patent A1-2,840,273, particularly good results are obtained with a solution which contains about 20% by weight of crude 1,2-benzisothiazolin-3-one in the form of the sodium salt and about 65% by weight of dipropylene glycol, and also about 15% by weight of water. In the examples mentioned in German Patent A1-2,840,273, the water content of the liquid formulations is between 7 and 12.1% by weight, and only in Example 3 is a water content of 27.1% by weight achieved, using methylcarbitol. For various reasons, however, it is desirable for such formulations to contain as little organic solvent as possible and instead as much water as possible.

It has now been found, surprisingly, that stable aqueous formulations of an alkali metal salt of 1,2-benzisothiazolin-3-one with a sufficient concentration of 1,2-benzisothiazolin-3-one can also be prepared without the hydroxylic organic solvents mentioned in German Patent A1-2,840,273, and at the same time the water content of the aqueous formulation can be increased to as least 30% by weight if the lithium salt is used as the alkali metal salt of 1,2-benzisothiazolin-3-one.

The invention relates to an aqueous formulation which contains an alkali metal salt of 1,2-benzisothiazolin-3-one and is characterized in that it contains the lithium salt of 1,2-benzisothiazolin-3-one and at least 30% by weight of water. The formulation according to the invention contains preferably at least 40% by weight, and especially preferably at least 50% by weight, of water and preferably at least 5% by weight, in particular at least 10% by weight, of the lithium salt of 1,2-benzisothiazolin-3-one.

According to the present invention, it is possible, for example, to prepare a purely aqueous solution of the lithium salt of 1,2-benzisothiazolin-3-one which, at a content of 10% by weight, based on the free 1,2-benzisothiazolin-3-one and on storage for 4 weeks at room temperature and also at 5° C. is stable, that is to say shows no precipitates, whilst in contrast, with an aqueous solution of the sodium salt of corresponding concentration, crystallization occurs on storage both at 5° C. and at room temperature. Even 20% strength purely aqueous solutions of the lithium salt of 1,2-benzisothiazolin-3-one are still stable at room temperature. The storage stability, especially of more highly concentrated solutions, at low temperatures can be increased further by adding 1,2-propylene glycol to the aqueous solutions of the lithium salt of 1,2-benzisothiazolin-3-one. This was also surprising, since no utilizable similar effect occurs in solutions of the sodium salt and 1,2-propylene glycol is therefore unsuitable as the sole addition of a solvent containing hydroxyl groups for an aqueous solution of the Na salt of 1,2-benzisothiazolin-3-one (compare German Patent A1-2,840,273, page 5, second paragraph). An aqueous solution, according to the invention, of the lithium salt containing 50% by weight of water, 30% by weight of 1,2-propylene glycol and 20% by weight of the lithium salt of 1,2-benzisothiazolin-3-one is stable both when stored for 4 weeks at room temperature and when stored at 5° C., whilst in contrast, a solution of the sodium salt of analogous composition exhibits crystallization both on storage at 5° C. and on storage at room temperature.

Purely aqueous formulations, according to the invention, of the lithium salt of 1,2-benzisothiazolin-3-one are prepared, for example, with a concentration of the lithium salt of 1,2-benzisothiazolin-3-one of at least 5% by weight, for example 5 to 25% by weight and preferably 5 to 20% by weight. They have a high storage stability.

The weight ratio of lithium salt of 1,2-benzisothiazolin3-one : water in such purely aqueous solutions is accordingly, for example, (5 to 25) : (95 to 75), and preferably (5 to 20) : (95 to 80).

The possibility of preparing purely aqueous formulations of 1,2-benzisothiazolin-3-one with a sufficient use concentration also offers ecological advantages, in addition to economic advantages, since pollution of the environment by organic solvents is eliminated.

The storage stability of highly concentrated aqueous solutions of the lithium salt of 1,2-benzisothiazolin-3-one can be improved at low temperatures by addition of organic solvents which are water-miscible.

As already mentioned, 1,2-propylene glycol, for example, is suitable as such a solvent. Other solvents which are suitable are, for example: lower alcohols, glycols, di- and triglycols, such as, for example, methanol, ethanol, propanol, ethylene glycol, diethylene glycol, triethylene glycol, glycol ethers, such as, for example, ethylene glycol monomethyl ether, ethylene glycol monoethyl ether, 1,2-propylene glycol monomethyl ether, diethylene glycol monomethyl ether, diethylene glycol monoethyl ether, diethylene glycol monopropyl ether and diethylene glycol monobutyl ether, or mixtures of such solvents.

Formulations according to the invention which have a high storage stability with a content of the lithium salt of 1,2-benzisothiazolin-3-one of, for example, 5 to 30% by weight can be prepared with water and solvent mixtures containing one or more organic water-miscible solvents.

The weight ratio of lithium salt of 1,2-benzisothiazolin3-one : water : water-miscible organic solvent can be, for example, (5 to 30) : (95 to 30) : (0 to 40), preferably (5 to 20) : (95 to 40) : (0 to 40). The formulations according to the invention with more than 25% by weight of lithium salt usually contain more than 5% by weight of a water-miscible organic solvent.

The aqueous formulations according to the invention can be prepared by a process in which the lithium salt of 1,2-benzisothiazolin-3-one is introduced into water or a mixture of water and one or more water-miscible organic solvents, advantageously with thorough mixing and/or with a slight increase in the temperature, and is then dissolved. The proportions are chosen here such that the formulations formed contain at least 30% by weight of water. It is also possible to use pure or crude 1,2-benzisothiazolin-3-one as the starting substance and to prepare the lithium salt therefrom.

Crude 1,2-benzisothiazolin-3-one is the crude product obtained in the preparation of 1,2-benzisothiazolin-3-one. To prepare aqueous solutions of the lithium salt, this crude product, for example in the form of the water-moist press-cake obtained in the preparation of 1,2-benzisothiazolin-3-one, or pure 1,2-benzisothiazoline-3-one is suspended in water, and equivalent amounts of a slight excess of up to, for example, 0.1 mol of lithium hydroxide and/or lithium carbonate and/or trilithium phosphate are added, advantageously with stirring and gentle warming to, for example, 30 to 40° C. Purely aqueous solutions of the lithium salt of 1,2-benzisothiazolin-3-one are directly obtained in this manner. The reverse procedure, that is to say the introduction of pure or crude 1,2-benzisothiazolin-3-one into aqueous solutions of lithium hydroxide and/or lithium carbonate and/or trilithium phosphate, likewise advantageously with stirring and gentle warming to, for example, 30 to 40° C., also leads to purely aqueous solutions according to the invention. If desired, a water-miscible organic solvent or solvent mixture is then also added.

Surprisingly, it has furthermore been found that the aqueous formulations according to the invention, which contain the lithium salt of 1,2-benzisothiazolin-3-one, have an in some cases clearly higher biological activity against some microorganisms, such as, for example, moulds, or some bacteria, such as, for example, *Escherichia coli*, in comparison with formulations which contain the sodium salt of 1,2-benzisothiazolin-3-one. It has been found, for example, that germination of spores of Aspergillus niger was considerably more inhibited after treatment with an aqueous formulation, according to the invention, containing the lithium salt of 1,2-benzisothiazolin-3-one than after treatment with a formulation containing the sodium salt of 1,2-benzisothiazolin-3-one. In determining the rate of destruction of Aspergillus niger, it was found that the samples treated with an aqueous formulation according to the invention containing the lithium salt of 1,2-benzisothiazolin-3-one have a lower germ count of up to a factor of 11 in the course of 3 days than samples which, in contrast, had been treated with a liquid formulation containing the sodium salt of 1,2-benzisothiazolin-3-one. The rate of destruction of the germs is also significantly higher with an aqueous solution of the lithium salt of 1,2-benzisothiazolin-3-one than with a solution of the sodium salt of 1,2-benzisothiazolin-3-one.

In addition to the surprisingly increased fungicidal activity, the aqueous formulations according to the invention exhibit a good antimicrobial action against gram-positive and gram-negative bacteria, yeasts and algae in a wide pH range, especially in the pH range from 4 to 12.

The aqueous formulations according to the invention are employed, in particular, as industrial preservatives and inter alia are used, for example, for protecting or preserving dispersions of polystyrene, polyacrylate and/or polyvinyl acetate, paints, boring and cutting oils, adhesives, compositions for coating paper, textile softeners, sizes based on starch, detergent bases, cleaning and polishing agents, spinning baths, leather finishes and emulsions of silicone and bitumen and for the treatment of industrial water in papermaking or industrial cooling water. The aqueous formulations according to the invention usually have pH values of 7 to 14, and in particular a pH from 8.5 to 12.5.

Depending on the field of use, it may be advantageous to add nonionic and/or anionic auxiliaries, such as emulsifying auxiliaries, dispersing auxiliaries and/or surfactants, which are known per se during or after the preparation of the aqueous formulations according to the invention. This measure may be necessary if acid or neutral pH values are established during use and dilution of the formulations according to the invention and it is desirable for the 1,2-benzisothiazolin-3-one which has partly precipitated at these pH values to be very finely distributed. Auxiliaries which are readily biologically degradable are preferred here. The amount of auxiliaries, such as emulsifying and/or dispersing auxiliaries and/or surfactants, added to usually not more than 5% by weight, based on the formulation. Emulsifying auxiliaries, dispersing auxiliaries, surfactants and the like can in some cases completely or partly replace the organic solvent in the formulations according to the invention.

It can furthermore be advantageous, for complexing of polyvalent cations, such as calcium or magnesium ions, to add complexing agents or water softeners which are known per se during or after the preparation. The amount of complexing agents or water softeners added is usually not more than 1% by weight, based on the formulation.

The complexing agents or water softeners, like the emulsifying or dispersing auxiliaries and/or surfactants, are also added during or after the preparation of the formulations according to the invention. The amount of the organic solvents used, where appropriate, is usually reduced by the amount of auxiliaries and/or complexing agents or water softeners used, where appropriate.

The present invention is illustrated in more detail by the following examples, parts and percentage contents being expressed by parts by weight and percentages by weight.

EXAMPLE 1

A solution of 48.3 g of lithium hydroxide monohydrate in 750 ml of water is added to 170.6 g of 1,2-benzisothiazolin3-one in the form of a 98.5% strength powder, a solution is obtained by stirring and warming to 30° to 40° C. and this solution is made up to 1 kg with water. The resulting aqueous solution is stable on storage at 0° to 5° C. and contain 16.8% of the lithium salt of 1,2-benzisothiazolin-3-one and 83.2% of water.

Comparison Example

An aqueous solution, prepared according to Example 1, of sodium 1,2-benzisothiazolin-3-one is not stable on storage; storage at 0° to 5° C. leads to deposition of 104 g of sodium 1,2-benzisothiazolin-3-one; the aqueous filtrate contains 8.8% of sodium 1,2-benzisothiazolin-3-one.

EXAMPLE 2

Instead of 170.6 g of 1,2-benzisothiazolin-3-one with a purity of 98.5%, 229.2 g of 1,2-benzisothiazolin-3-one with a purity of 94.5% and 60.8 g of lithium hydroxide monohydrate are employed in accordance with the procedure of Example 1. After a final weight of 1 kg has been established, an aqueous solution containing 22.5% of lithium 1.2-benzisothiazolin-3-one and 77.5% of water is obtained.

Further examples of aqueous formulations, according to the invention, of lithium 1,2-benzisothiazolin-3-one (I) are to be found in the following table, the concentration of lithium 1,2-benzisothiazolin-3-one being given in column 2 and the solvent and any auxiliaries added being given in column 3.

TABLE 1

| Example | Concentration of (I) (%) | Solvent and any auxiliary present | (%) |
|---|---|---|---|
| 3 | 25 | ®Emulsogen EL (1) | 2 |
|   |    | water | 73 |
| 4 | 27.5 | ®Arkopal N 080[2] | 5 |
|   |      | water | 67.5 |
| 5 | 28 | ®Genapol X 080[3] | 4 |
|   |    | water | 68 |
| 6 | 24 | ®Hostapur SAS 93[4] | 1 |
|   |    | water | 75 |
| 7 | 21 | ®Aquamollin BC highly concentrated[5] | 0.5 |
|   |    | water | 78.5 |
| 8 | 20 | 1,2-propylene glycol | 30 |
|   |    | water | 50 |
| 9 | 25 | 1,2-propylene glycol | 20 |
|   |    | ®Humectol C highly concentrated[6] | 1 |
|   |    | water | 54 |

[1] ® Emulsogen is a registered trademark of Hoechst AG, Frankfurt am Main 80. ® Emulsogen EL is an emulsifier based on a fatty acid polyglycol ester.

TABLE 1-continued

| Example | Concentration of (I) (%) | Solvent and any auxiliary present | (%) |
|---|---|---|---|

[2] ® Arkopal is a registered trademark of Hoechst AG. ® Arkopal NO 80 is a nonionic surfactant based on a nonylphenol polyglycol ether.

[3] ® Genapol is a registered trademark of Hoechst AG. Genapol X 080 is a fatty alcohol polyglycol ether.

[4] ® Hostapur is a registered trademark of Hoechst AG. ® Hostapur SAS 93 is a biologically degradable alkanesulphonate.

[5] ® Aquamollin is a registered trademark of Cassella AG, Frankfurt am Main 61. ® Aquamollin BC highly concentrated is a water softener based on ethylenediaminetetraacetic acid.

[6] Humectol is a registered trademark of Cassella AG. ® Humectol C highly concentrated is a wetting agent based on a sulphonated oleic acid amide derivative.

EXAMPLE 11

The rates of destruction of Aspergillus niger are determined on aqueous solutions of the lithium salt and of the sodium salt of 1,2-benzisothiazolin-3-one, both of which contain 0.0016% by weight of 1,2-benzisothiazolin-3-one. For this, a germ suspension of Aspergillus niger is pipetted into the solution to be tested and, after certain periods of time, the germ count is measured by the Koch plate casting method (see, for example, K.H. Wallhäusser in "Praxis der Sterilisation, Desinfektion, Konservierung" ("Practice of Sterilization, Disinfection and Preservation"), G. Thieme Verlag, Stuttgart, 1984).

The germ suspension is obtained in a known manner by flotation of a stock culture of Aspergillus niger with physiological saline solution and dilution of the flotation mixture with physiological saline solution and distribution.

The values shown in Table 2 were found. In contrast, after 5 minutes 365 germs and 72 hours 295 germs per $ml \times 10^{-3}$ were counted in a growth control in distilled water.

TABLE 2

Determination of the rate of destruction of Aspergillus niger using an Li and an Na salt solution of 1,2-benzisothiazolin-3-one

| | Number of germs per ml $\times 10^{-3}$ after | | | |
|---|---|---|---|---|
| | 5 minutes | 24 hours | 48 hours | 72 hours |
| Na salt solution | 345 | 123 | 51 | 22 |
| Li salt solution | 275 | 91 | 10.2 | 1.95 |
| Factor = $\frac{Line\ 1}{Line\ 2}$ | 1.25 | 1.35 | 5 | 11.28 |

The Li salt solution and Na salt solution tested are both 0.0016% strength in respect of the 1.2-benzisothiazolin-3-one.

What is claimed is:

1. An aqueous formulation containing the lithium salt of 1,2-benzisothiazolin-3-one, water and a water-miscible organic solvent in a weight ratio of 5 to 30 : 95 to 30 : 0 to 40, respectively, said formulation prepared by reacting lithium hydroxide lithium carbonate or trilithium phosphate in water or in a water miscible organic solvent with 1, 2-benzisothiazolin -3-one.

2. The formulation according to claim 1 wherein the water-miscible organic solvent is 1,2-propylene glycol.

3. The formulation according to claim 1 which comprises said lithium salt, water and a water-miscible organic solvent in a weight ratio of 5 to 20 : 95 to 40 : 0 to 40.

4. The formulation according to claim 3 wherein the water-miscible organic solvent is 1,2-propylene glycol.

5. The formulation according to claim 1 which contains at least one a dispersing auxiliary in amounts of up to 5% by weight.

6. The formulation according to claim 1 which contains a complexing agent of a water softener in amounts of up to 1% by weight.

7. A method of protecting aqueous solutions from infestation by Aspergillus niger which comprises adding a biocidally effective amount of the formulation of claim 1 to said solutions.

8. The method according to claim 7 wherein the amount of said formulation is such that the aqueous solution protected contains at least about 0.0016% by weight of the lithium salt of 1,2-benzisothiazolin-3-one.

* * * * *